(12) United States Patent
Stark et al.

(10) Patent No.: US 8,524,635 B2
(45) Date of Patent: Sep. 3, 2013

(54) ANTIFUNGAL COMPOSITION

(75) Inventors: Jacobus Stark, Rotterdam (NL);
Ferdinand Theodorus Jozef Van Rijn, Delft (NL); Wilhelmus Maria Van Der Krieken, Wageningen (NL); Lucas Henricus Stevens, Utrecht (NL)

(73) Assignees: DSM IP Assets B.V., Heerlen (NL);
Ceradis B.V., Wageningen (NL)

( * ) Notice: Subject to any disclaimer, the term of this patent is extended or adjusted under 35 U.S.C. 154(b) by 666 days.

(21) Appl. No.: 12/373,622

(22) PCT Filed: Jul. 16, 2007

(86) PCT No.: PCT/EP2007/057330
§ 371 (c)(1),
(2), (4) Date: Nov. 2, 2009

(87) PCT Pub. No.: WO2008/009657
PCT Pub. Date: Jan. 24, 2008

(65) Prior Publication Data
US 2010/0050512 A1 Mar. 4, 2010

(30) Foreign Application Priority Data

Jul. 17, 2006 (EP) .................................... 06117331

(51) Int. Cl.
*A01N 43/90* (2006.01)
*A01N 59/26* (2006.01)
*A01P 3/00* (2006.01)

(52) U.S. Cl.
USPC ............. 504/100; 514/31; 424/601; 424/602; 424/605; 424/606

(58) Field of Classification Search
USPC .................. 424/601, 605, 606, 602; 514/31; 504/100
See application file for complete search history.

(56) References Cited

U.S. PATENT DOCUMENTS

| | | |
|---|---|---|
| 4,148,891 A | 4/1979 | Smink |
| 5,552,151 A | 9/1996 | Noordam et al. |
| 5,597,598 A | 1/1997 | Van Rijn et al. |
| 5,962,510 A | 10/1999 | De Haan et al. |
| 6,150,143 A | 11/2000 | Raghoenath et al. |
| 6,655,081 B1 | 12/2003 | Stark et al. |
| 7,816,332 B2 | 10/2010 | Stark et al. |
| 2003/0026797 A1 | 2/2003 | Beudeker |
| 2007/0264394 A1 | 11/2007 | Dutreux et al. |
| 2008/0234210 A1 | 9/2008 | Rijn et al. |
| 2010/0050299 A1 | 2/2010 | Stark et al. |
| 2010/0204168 A1 | 8/2010 | Haan et al. |
| 2010/0234313 A1 | 9/2010 | Hee et al. |
| 2010/0292315 A1 | 11/2010 | Van Hee et al. |
| 2010/0297311 A1 | 11/2010 | Van Gurp et al. |
| 2011/0047654 A1 | 2/2011 | Stark et al. |
| 2011/0059914 A1 | 3/2011 | Haan et al. |
| 2012/0027905 A1 | 2/2012 | Stark et al. |
| 2012/0052166 A1 | 3/2012 | Hooft et al. |

FOREIGN PATENT DOCUMENTS

| | | |
|---|---|---|
| EP | 0 678 241 | 10/1995 |
| FR | 2 819 992 | 8/2002 |
| RO | 80510 | 7/1979 |
| WO | WO 2004/067699 | 8/2004 |
| WO | WO 2004/105491 | 12/2004 |
| WO | WO 2006/136551 | * 12/2006 |

OTHER PUBLICATIONS

Webster's New World Dictionary, second college ed., The World Publishing Co., NY, 1972, p. 1127.*
Farm Chemicals Handbook '98, Meister Publishing Co., Ohio, 1998, p. C 191.*
HCAPLUS abstract 1998:638576 (1998).*
International Search Report for PCT/EP2007/057330, mailed Mar. 7, 2008.
International Preliminary Report on Patentability for PCT/EP2007/057330, dated Oct. 10, 2008.
Database WPI, Accession No. 1983-762767, TUDOREL BAICU: Compsn. for fighting tuber and tuber-bulb rot—contg. Mancozeb combined with benomil, methyl thiophanate or thia-bendazole and tetracycline or chlor-amphenicol, * RO 80 510, (Jul. 30, 1979).

* cited by examiner

*Primary Examiner* — John Pak
(74) *Attorney, Agent, or Firm* — Baker Donelson Bearman Caldwell & Berkowitz, PC

(57) ABSTRACT

The present invention relates to a process for the treatment of an agricultural product which comprises the addition of a composition which comprises phosphite and natamycin to the agricultural product wherein the composition comprises preferably less than 0.1 g lignosulphonate, more preferably less than 0.1 g polyphenol, per gram natamycin and is still more preferably free of lignosulphonate and most preferably free of polyphenol.

23 Claims, No Drawings

ANTIFUNGAL COMPOSITION

This application is the U.S. national phase of International Application No. PCT/EP2007/057330, filed 16 Jul. 2007, which designated the U.S. and claims priority to Europe Application No. 06117331.6, filed 17 Jul. 2006, the entire contents of each of which are hereby incorporated by reference.

FIELD OF THE INVENTION

The present invention relates to novel antifungal compositions for the treatment of agricultural crops such as flower bulbs, tubers, root-tubers, rootstocks, onions and seed-potatoes.

BACKGROUND OF THE INVENTION

The cultivation of bulbous and tuberous plants is a difficult process. Mostly after harvesting the bulbs or tubers are stored for prolonged periods of several months before they are planted in the earth again. After re-planting mostly it takes several weeks up to several months before the plant develops. Furthermore, most of these crops are grown in the open air, where all kind of negative influences determine the development of the crop, e.g., moulds, insects, parasites and weather conditions such as a too high humidity. Also during storage and transport the quality of the bulbs or tubers can be affected in a negative way. To avoid deterioration of the bulbs or tubers, they are mostly stored under more or less controlled environmental conditions.

Although bulbs and tubers are subjected to various biotic and abiotic threats, development of moulds during storage and after planting can be considered as one of the main problems. Only in The Netherlands the economic losses due to mouldiness of flower bulbs is estimated at € 200 million per year, this in spite of the extensive use of synthetic fungicides.

On flower bulbs of which tulip and lily are the most important crops *Fusarium* (e.g., *Fusarium oxysporum*) and *Penicillium* species are known to cause most of the problems. However, on these and other bulbs also other moulds such as *Botrytis* species, *Stagnospora* species, *Rhizoctonia* species and *Pythium* species may occur. On seed-potatoes *Fusarium* species (e.g., *Fusarium solani*), *Rhizoctonia solani*, *Helminthosporium solani*, *Phoma* species and *Penicillium* species are examples of well known pathogenic moulds.

Since due to upcoming EU regulation it is expected that some of the frequently used synthetic fungicides will be banned, the future problems concerning moulds are expected to become even worse. To prevent considerable economic losses for the industry in the near future, there is a need for environmental friendly natural fungicides. Also from an environmental and health point of view it is of importance to obtain alternatives for the harmful synthetic fungicides which are applied nowadays.

For many decades the polyene macrolide antimycotic natamycin has been used to prevent fungal growth on food products such as cheeses and sausages. This natural preservative, which is produced by fermentation using *Streptomyces natalensis*, is widely used throughout the world as a food preservative and has a long history of safe use in the food industry. It is very effective against all known food spoilage moulds. Although natamycin is applied for many years in e.g. the cheese industry up to now development of resistant mould species was never observed.

Cheeses and sausages are treated by immersion or by spraying with a suspension of natamycin in water. Cheeses can also be covered by an emulsion of a plastic coating of mostly polyvinyl acetate in water containing natamycin. Casings applied on sausages can be soaked in a saturated suspension of natamycin. In case of beverages such as fruit juices, natamycin is simply dissolved in the end product.

Natamycin has a low solubility in water of 30-50 ppm; only the dissolved fraction has antifungal activity. Since natamycin has a MIC (Minimal Inhibitory Concentration) of less than 10 ppm for most fungi, the dissolved concentration is in most cases sufficient to prevent mould development. Under normal hygienic conditions denaturation of dissolved natamycin is compensated by dissolution of natamycin from the crystals and diffusion over the surface to the site of contamination.

Already in the 1970ties it was realized that natamycin (pimaricin) might be of value for control of fungal plant diseases on flower bulbs (see Dekker and Langerak (1979)). It was demonstrated that natamycin was as effective as organic mercury or formalin in preventing the spread of *Fusarium oxysporum* in the water baths in which the bulbs were dipped for two hours at 43.5° C. to eliminate nematodes, insects and mites. Natamycin effectively eliminated the *Fusarium* mould preventing cross contamination from diseased to healthy bulbs in the water bath.

However, in spite of these positive results of thirty years ago and the observation that under laboratory conditions natamycin was effective in combating fungal species occurring on crops such as flower bulbs, tubers and seed-potatoes, in practice treatment of these crops with even high natamycin concentrations was not effective in preventing mould development. Therefore, up to now this environmental friendly antifungal agent was never applied in practise on e.g. flower bulbs and comparable mould-sensitive crops such as tubers, onions and seed-potatoes.

In patent application WO 2004/067699 it is disclosed that a composition containing lignosulphonates together with a wide selection of other compounds can protect agricultural crops against threats such as weeds, biotic and abiotic stresses, insects, nematodes and pathogenic micro-organisms such as moulds, bacteria and viruses. Polyphenols and especially lignosulphonates are applied to enhance the effectiveness of other active compounds such as pesticides, fungicides, herbicides and plant protection compounds. Natamycin is mentioned as an example of a suitable fungicide, while potassium phosphite is mentioned as an example of a plant protection compound. In Example 3 of WO 2004/067699 it is demonstrated that the combination natamycin-lignosulphonate was effective against *Botrytis* development on leaf tips. In Example 11 an experiment is described in which lignosulphonate and natamycin were used to protect tulips against the *Fusarium* mould. It is observed that the leaves growing from tulip bulbs treated with natamycin and lignosulphonate showed no yellow mould spots compared with the bulbs dipped in natamycin alone where some yellow spots were observed. However, in this experiment the quality of the bulbs was not reported.

SUMMARY OF THE INVENTION

The present invention relates to a process for the treatment of an agricultural product which comprises the addition of a composition which comprises phosphite and a polyene fungicide to the agricultural product. Preferably, the composition comprises 0.1 g or less lignosulphonate, more preferably 0.1 g or less polyphenol, per gram polyene fungicide and is still more preferably free of lignosulphonate and most preferably free of polyphenol.

The present invention also provides a composition comprising phosphite and natamycin. The ratio of phosphite to natamycin (in weight) in the composition is in general between 2:1 to 500:1 (w/w), preferably between 3:1 to 300:1 (w/w) and more preferably between 5:1 to 200:1 (w/w). Preferably, in the composition 10 times (or more than 10 times) less (in gram) lignosulphonate, more preferably 10 times (or more than 10 times) less (in gram) polyphenol, is present than natamycin and still more preferably the composition is free of lignosulphonate and most preferably is free of polyphenol. This composition can be used to treat agricultural products.

DETAILED DESCRIPTION OF THE INVENTION

The present invention provides a process for the treatment of an agricultural product which comprises the addition of a composition which comprises phosphite and a polyene fungicide to the agricultural product, wherein the composition comprises 0.1 g or less lignosulphonate, preferably 0.1 g or less polyphenol, per gram polyene fungicide. More preferably, the composition comprises 0.05 g or less lignosulphonate, preferably 0.05 g or less polyphenol, per gram polyene fungicide. Even more preferably, the composition comprises 0.01 g or less lignosulphonate, preferably 0.01 g or less polyphenol, per gram polyene fungicide. In a preferred embodiment the composition of the invention is free of lignosulphonate and most preferably free of polyphenol.

Unexpectedly the present inventors have found that the protection of e.g. bulbs, tubers and seed-potatoes against moulds is markedly enhanced when a polyene fungicide, e.g. natamycin, is combined with a natural crop protection compound belonging to the group of phosphites, e.g $KH_2PO_3$ or $K_2HPO_3$ or a mixture of both phosphite salts. Moreover, it has been found that the growth and development of the crops is improved and the yield is increased. It has also been found that lignosulphonate has no or even a positive effect on mould formation on agricultural products, such as flower bulbs. Therefore, substantially no polyphenols such as lignosulphonates are present in the composition of the invention or are present in the process according to the present invention to protect agricultural products against moulds.

The present invention provides a preparation or a composition for the treatment of agricultural products such as flower bulbs, tubers, root-tubers, rootstocks, onions and seed-potatoes, comprising an amount of polyene fungicide and an amount of a phosphite compound effective to prevent the development of moulds. Preferably, the antifungal activity consists of the activity of a polyene fungicide combined with a phosphite salt.

Suitable examples of polyene fungicides applied in the composition of the invention are natamycin, nystatin, amphotericin B, filipin and lucensomycin. The preferred polyene fungicide is natamycin. In an embodiment of the invention the compositions may also contain two or more different polyene fungicides. It is to be understood that derivatives of polyene fungicides including, but not limited to, salts or solvates of polyene fungicides or modified forms of polyene fungicides may also be applied in the compositions of the invention. Commercial products which contain natamycin such as Delvocid® can be incorporated in a composition of the invention. Delvocid® is the brand name of a commercial product produced by DSM Food Specialties (The Netherlands). Delvocid® contains 50% (w/w) of natamycin.

Suitable examples of phosphite compounds are potassium phosphites such as $KH_2PO_3$ and $K_2HPO_3$, sodium phosphites, ammonium phosphites, ethyl hydrogen phosphonate, fosetyl-aluminium complexes, phosphorous acid or its alkali metal or alkaline earth metal salts, or mixtures of these compounds. A mixture of e.g. $KH_2PO_3$ and $K_2HPO_3$ can easily be obtained by e.g. adding KOH or $K_2CO_3$ to a final pH of 5.0-6.0 to a $KH_2PO_3$ solution. Precursor-type compounds which in the bulb, seed-potato, crop or plant are metabolized into phosphite compounds can also be included in the compositions of the present invention. Such compositions and their use in the process as described herein are another aspect of the present invention. Examples are phosphonates such as the fosetyl-aluminium complex. In e.g. a plant the ethyl phosphonate part of this molecule is metabolized into a phosphite. An example of such a compound in the commercial ethyl hydrogen phosphonate product called Aliette® (Bayer, Germany).

A composition of the present invention may be a solid, e.g. a powder, or a liquid. Generally, it will be a liquid which can be used for immersion or spraying e.g. the flower bulbs, tubers, onions and seed-potatoes. A composition of the present invention will generally comprise 0.05 g/l to 100 g/l and preferably 0.1 g/l to 50 g/l of a polyene fungicide. Preferably, the amount is from 0.1 g/l to 3 g/l. Preferably, the polyene fungicide is natamycin. The composition will generally comprise 0.5 g/l to 100 g/l and preferably 1 g/l to 50 g/l potassium phosphite. More preferably, the amount of potassium phosphite is from 2 g/l to 30 g/l. According to the present invention also other phosphites may be used in equimolar amounts to the potassium phosphite.

The composition of the invention may optionally contain a sticking agent, which improves the sticking of the antifungal compound to the surface of e.g. the flower bulb, tuber, cutting, onion or seed-potato. Examples of such sticking agents are latex based products like Prolong® (Holland Fyto B.V., The Netherlands) and Bond® (Loveland Industries Ltd), pinolene/terpene based products like Nu-film® (Hygrotech Saad) and Spray-Fast® (Mandops) and long chain polysaccharides like xanthan gum and guar gum. Alternatively, the sticking agents may be polymers or co-polymers from types of polymers such as polyacrylate and polyethylene.

For treating objects with a hydrophobic surface such as e.g. flower bulbs, the addition of a surfactant may be of advantage. The optional addition of said compounds is also included in this invention. Examples of useful surfactants are anionic tensides such as sodium lauryl sulphate or polyethylene alkyl ethers or polyoxyethylethers, e.g. Tween® 60, 61 or 65. Other examples of useful surfactants are organo silicones, sulfosuccinates, alcohol ethoxylates, fatty acid ethoxylates, fatty acid propoxylates and the commercial product Zipper® (Asepta BV, The Netherlands). In addition, the compositions may also contain suitable carriers and adjuvants ordinarily employed in formulation technology, including, but not limited to, mineral substances, solvents, dispersants, wetting agents, stabilisers, antifoaming agents and antioxidants.

To improve the effectiveness and the practical use of the present invention also compounds to combat insects, nematodes, mites and bacteria may be added to the antifungal composition. Examples of such compounds are Admire® (Bayer), formalin and Actellic® (Syngenta, Switserland). In addition, the composition of this invention may also contain other antifungal compounds such as e.g. captan (nonsystemic phthalimide fungicide), prochloraz (N-propyl-N-[2-(2,4,6-trichlorophenoxy)ethyl]imidazole-1-carboxamide) and formalin and commercial products known under the name Topsin® M (Cerexagri Inc, active ingredient thiofanaat-methyl), Jet-5® (Certis Europe BV, The Netherlands, active ingredients peracetic acid and hydrogenperoxide) and Shirlan® (Syngenta, Switserland, active ingredient fluazinam).

The compositions of the present invention also include concentrated stock suspensions/solutions and concentrated dry products such as e.g. powders, granulates and tablets. They can be used to prepare compositions for immersion or spraying of the agricultural products.

Furthermore, the invention provides agricultural products treated with a composition of the present invention. The treated agricultural products may contain a coating comprising a composition of the invention. Examples of such agricultural products are bulbs, especially flower bulbs such as tulip, lily, narcissus, crocus or hyacinth; other bulbous crops such as e.g. onions; tubers, root-tubers and rootstocks, such as seed-potatoes and dahlia.

Said crops can be treated after harvesting before storage e.g. by immersion or spraying with a composition of the present invention. When treated just, e.g. directly, after harvesting, moulding e.g. mould growth of e.g. the flower bulbs during storage will be prevented. For example, bulbs of tulips are generally harvested in summer and planted in October-November. Other examples are lily bulbs and seed-potatoes, these crops are harvested in summer or autumn and planted in springtime.

Alternatively, the bulbs, tubers or seed-potatoes can also be treated with a composition of the present invention just before planting. This will give an extra protection of the crops during germination in the ground.

Up to now bulbs such as flower bulbs were treated with fungicides just before planting. Surprisingly, we have found that when bulbs are treated with an antifungal agent before storage, preferably directly after harvesting, an optimal control of moulds is achieved. Directly after harvesting as used herein means during washing/cleaning, just after washing before the first drying step (before peeling) or after peeling before the second drying step, e.g. within the first 14 days, preferably within the first 12 days, more preferably within the first 10 days, particularly within the first 7 days and more particularly within the first 5 days after harvesting. So, a further aspect of the present invention pertains to a process for the prevention and/or treatment of bulbs from moulding, i.e. mould/fungal growth and/or mould/fungal infection, said process comprising the step of applying an antifungal agent or an antifungal composition to bulbs directly after harvesting of the bulbs. In a preferred embodiment the antifungal composition comprises natamycin. Suitable antifungal compositions, include, but are not limited to, compositions comprising compounds such as e.g. captan (nonsystemic phthalimide fungicide), prochloraz (N-propyl-N-[2-(2,4,6-trichlorophenoxy)ethyl]imidazole-1-carboxamide) and formalin and commercial products known under the name Topsin® M (Cerexagri Inc, active ingredient thiofanaat-methyl), Jet-5® (Certis Europe BV, The Netherlands, active ingredients peracetic acid and hydrogenperoxide) and Shirlan® (Syngenta, Switserland, active ingredient fluazinam). In a preferred embodiment the compositions of the present invention are being applied in the process. A person skilled in the art will appreciate that antifungal compositions may comprise different antifungal agents and may further comprise other agents/compounds suitable for the intended use.

In addition, the compositions of the present invention may be used on cuttings or grafts such as generally applied to multiply flower plants, indoor plants or crops; seeds for growing of new plants and treatment of seeds that are stored as feed or feed (e.g. maize and wheat). Examples of cuttings or grafts are carnation, fuchsia, chrysanthemum, roses, fruit plants like tomato, melon, cucumber, and aubergine and plants grown in greenhouses.

The composition of the invention may also be used to prevent mould/fungal growth and/or mould/fungal infection on stored agricultural products such as grain, maize, coffee, beans, cocoa beans, soy beans, berries such as e.g. strawberries, citrus fruits such as e.g. oranges, grapefruits and lemons, grapes, peaches, plums and cherries. Of course, the composition of the invention may also be used during the drying and/or fermentation process of coffee and cocoa beans.

Finally, the composition of the present invention may also be used for the treatment of growing crops in the field including, but not limited to, cereal crops such as grain and maize, vegetables, coffee plants, cocoa plant, fruit trees, grape plants, strawberries, cucumber plants and tomato plants.

The present invention is also concerned with the use of a composition according to the invention to prevent agricultural products from moulding and/or to treat agricultural products against moulding, i.e. mould/fungal growth and/or mould/fungal infection.

Examples

Example 1

Treatment of Tulip Bulbs

In this example tulip bulbs of the variety Prominence were treated with a 1:1 mixture of spores of the pathogenic moulds *Fusarium oxysporum* f. sp. *tulipae* CBS116591 and *Fusarium oxysporum* f. sp. *tulipae* Tu467 by submersing the bulbs for 30 minutes in a suspension containing 50.000-100.000 spores per ml. The mould spores were obtained using well-known methods. It should be noticed that in this challenge test the effect of the compositions was tested under very severe circumstances, because a very high number of mould spores was used. In real practise, the disease pressure will be less severe.

After the inoculation with mould spores the bulbs were dried following well-known methods. 40-60 minutes after drying the bulbs were treated with the different compositions described in Table 1. The compositions were prepared according to the instructions described on the label. All compositions contained 0.1% (v/v) of the sticking agent Prolong® (Holland Fyto, The Netherlands) and the surfactant Zipper® (Asepta BV, The Netherlands) in a concentration of 1 ml/l. Subsequently, the bulbs were planted in soil in pots (10 bulbs per pot) and incubated under well known standard conditions for growing tulips.

Table 1 shows the percentage of infected bulbs for each treatment. The bulbs were examined for mould infection when the flowers were at full bloom. For each incubation the average observation of 60 bulbs is given. Statistical analysis was performed after an ASIN transformation. The LSD at P=5% was 6.50.

The results in Table 1 clearly demonstrate that the composition of this invention (natamycin+potassium phosphite) gives a much better protection against moulds than natamycin or potassium phosphite alone. Surprisingly, the combined application of natamycin and potassium phosphite leads to a strong synergistic reduction in infection. The results presented in Table 1 also demonstrate that copper lignosulphonate as such or in combination with natamycin did not lead to reduction of moulds, but even to a small increase in mould infection. Apparently, copper lignosulfonate has a negative effect on the activity of combined application of potassium phosphite and/or natamycin when applied on flower bulbs.

Example 2

Treatment of Tulip Bulbs

This example describes the results of an experiment performed as described in Example 1. Just as in the experiment performed in Example 1, the pH of all solutions was adjusted to 5.7 with KOH or $K_2CO_3$ which results in a mixture of two phosphites, $KH_2PO_3$ and $K_2HPO_3$.

The results obtained with a composition comprising 25% of a standard cocktail which is generally applied in practice are included. This standard cocktail contains the commercial products 0.5% (v/v) Captan (546 gram active ingredient per liter), 0.3% (v/v) Prochloraz (450 g/l) and 1% (v/v) Topsin M (500 g/l). The number of infected bulbs was scored and grouped using the well-known statistical method ANOVA (LSD at P=5% was 6.50).

Table 2 shows that the composition of this invention is ranked in the same group as the combination of natamycin and standard cocktail, meaning that the environmental friendly composition of natamycin and potassium phosphite could replace a combination of natamycin with the standard cocktail of fungicides. This example also illustrates that the composition of this invention gives a much better protection against moulds than the standard cocktail, natamycin or potassium phosphite alone. "D" is the control, untreated bulbs.

Example 3

Treatment of Tulip Bulbs

In this experiment tulip bulbs of the variety Prominence were infected just after harvesting with a spore suspension of *Fusarium oxysporum* f. sp. *tulipae* CBS 116593 and treated with the antifungal compositions presented in Table 3. This time, the bulbs were not planted but stored. In this experiment the efficacy of the antifungal composition during the storage of the bulbs was studied.

After harvesting, the outer dry skin of the bulbs was removed and the bulbs were disinfected by applying a treatment with 4% (v/v) Glorix® for 5 minutes. The bulbs were dried and a lesion of a few millimeters was made in the surface of the bulb using a knife. The wound was infected with 15 µl of a spore suspension of *Fusarium oxysporum* f. sp. *tulipae*; this way approximately 10.000 mould spores infected the wound after which the bulbs were treated with 30 µl of the compositions described in Table 3. Twenty bulbs were treated per composition. In one experiment the treatment with the antifungal composition was applied 12 hours after infection. The bulbs were incubated for 15 days at a temperature of 24° C. after which the bulbs were examined visually on mould growth. The results are presented in Table 3.

The results clearly demonstrate that the composition of this invention protects flower bulbs against mould infection during storage. It also demonstrates that when the treatment is applied 12 hours after infection, the composition of this invention even fully prevents moulding of the bulbs.

These results also demonstrate that treatment of bulbs with an antifungal composition directly after harvesting of the bulbs and before storage prevents moulding of the bulbs.

Example 4

Treatment of Seed-Potatoes

This example illustrates the antifungal effect of a composition comprising natamycin and potassium phosphite on seed-potatoes against the mould *Helminthosporium solani* which is causing the well-known silver scurf disease on potatoes.

Freshly harvested seed-potatoes naturally contaminated with silver scurf were selected for this experiment. The seed-potatoes were treated with the compositions described in Table 4. All compositions contained 0.1% (v/v) of the sticking agent Prolong® (Holland Fyto, The Netherlands) and the surfactant Zipper® (Asepta BV, The Netherlands) in a concentration of 1 ml/l. Said compositions were sprayed on the seed-potatoes using well-known methods after which the seed-potatoes were stored under standard conditions. For each composition 9×25 seed-potatoes were used; of each composition one triple set of seed-potatoes (3×25) was judged visually on mould growth after 1 month of storage (t=1), after 3 months of storage (t=3) and after 6 months of storage (t=6). The mould growth is reported as increase of surface covered with moulds (in percentage). In addition the sporulation of the moulds on the seed-potatoes was examined and scored on a scale from 0 to 4 (0=no sporulation; 4=high sporulation). These results are presented in Table 5.

The results presented in Tables 4 and 5 clearly demonstrate that the composition of this invention is very effective in inhibiting the silver scurf mould during the storage for six months of seed-potatoes. It is also demonstrated that the composition comprising natamycin and potassium phosphite almost completely prevents sporulation of the mould during storage and by this way prevents further contamination during storage of the seed-potatoes.

TABLE 1

Percentage of mould infected tulip bulbs after different treatments.

| Active ingredient | % of bulbs infected |
| --- | --- |
| control | 100 |
| natamycin (0.2 g/l) | 88 |
| natamycin (0.5 g/l) | 90 |
| potassium phosphite (20 g/l) | 87 |
| copper lignosulphonate (2 g/l) | 97 |
| Mix of natamycin (0.2 g/l) and copper lignosulphonate (2 g/l) | 100 |
| Mix of natamycin (0.5 g/l) and copper lignosulphonate (2 g/l) | 95 |
| Mix of natamycin (0.5 g/l) and potassium phosphite (20 g/l) | 42 |

TABLE 2

Statistical evaluation of mould infection of tulip bulbs treated with different antifungal compositions.

| Component 1 | Component 2 | Score | Grouping |
| --- | --- | --- | --- |
| Control (untreated) | — | 90.0 | D |
| 120 mM phosphite | — | 72.9 | C |
| 200 ppm natamycin | — | 76.0 | C |
| 500 ppm natamycin | — | 75.0 | C |
| standard cocktail | — | 51.5 | B |
| 200 ppm natamycin | standard cocktail | 38.5 | A |
| 500 ppm natamycin | standard cocktail | 38.9 | A |
| 200 ppm natamycin | 120 mM phosphite | 43.3 | A |
| 500 ppm natamycin | 120 mM phosphite | 39.9 | A |

TABLE 3

Infection of tulip bulbs after 15 days of storage.

| Composition | Amount of bulbs with visible moulds (in %) | Amount of non-infected bulbs (in %) |
|---|---|---|
| Control (untreated) | 60 | 40 |
| 120 mM phosphite | 50 | 50 |
| 500 ppm natamycin | 40 | 60 |
| 500 ppm natamycin and 120 mM phosphite | 30 | 70 |
| 500 ppm natamycin and 120 mM phosphite (12 hours a.i.) | 0 | 100 |

TABLE 4

Increase in percentage of the surface of seed-potatoes covered with mould.

| Treatment | t = 1 | t = 3 | t = 6 |
|---|---|---|---|
| Water (control) | 3.8 | 3.4 | 7.8 |
| Phosphite 120 mM | 2.5 | 4.0 | 6.9 |
| Natamycin 2000 ppm | 1.5 | 3.0 | 3.8 |
| Natamycin 5000 ppm | 0.8 | 2.6 | 3.5 |
| Natamycin 2000 ppm and phosphite 120 mM | 0.8 | 2.5 | 1.2 |
| Natamycin 5000 ppm and phosphite 120 mM | 1.2 | 2.5 | 1.5 |

TABLE 5

Sporulation of silver scurf moulds on seed potatoes.

| Treatment | t = 1 | t = 3 | t = 6 |
|---|---|---|---|
| Water (control) | 2.7 | 1.8 | 2.4 |
| Natamycin 2000 ppm | 0.8 | 1.1 | 1.8 |
| Natamycin 5000 ppm | 0.6 | 1.2 | 0.7 |
| Phosphite 120 mM | 1.3 | 1.0 | 1.3 |
| Natamycin 2000 ppm and phosphite 120 mM | 0.3 | 0.3 | 0.1 |
| Natamycin 5000 ppm and phosphite 120 mM | 0.3 | 0.2 | 0.1 |

REFERENCES

Dekker J and Langerak C J (1979), Use of antifungal antibiotics in agriculture, with special reference to control of narcissus bulb rot with pimaricin. Abh. Akadamie. Wissenschaft. DDR, Abt. Math., Naturwiss., Tech. 2N:63-74.

The invention claimed is:

1. A composition, comprising:
   (a) natamycin, and
   (b) a further fungicide that is at least one selected from the group consisting of phosphorous acid, phosphite, and mixtures thereof, wherein the phosphite is selected from the group consisting of potassium phosphite, sodium phosphite, ammonium phosphite, an alkali metal salt of phosphorous acid, and an alkaline earth metal salt of phosphorous acid,
   wherein said natamycin, phosphorous acid, phosphite, and mixtures thereof are the only fungicides present in the composition.

2. A composition according to claim 1, characterized in that phosphite is present and the ratio of natamycin to phosphite is 1:2 to 1:500 (w/w).

3. A composition according to claim 1, characterized in that it has 10 times or more than 10 times less (in gram) lignosulphonate than natamycin.

4. A composition according to claim 1, characterized in that it has 10 times or more than 10 times less (in gram) polyphenol than natamycin.

5. A composition according to claim 1, characterized in that it further comprises one or more compounds selected from the group consisting of a sticking agent, a surfactant, and a compound to combat insects, nematodes, mites and/or bacteria.

6. A composition according to claim 1, characterized in that it further comprises a mineral substance, a solvent, a dispersant, a wetting agent, a stabiliser, an antifoaming agent or an antioxidant.

7. A process for the treatment of an agricultural product which comprises adding a composition according to claim 1 to the agricultural product.

8. An agricultural product treated with a composition according to claim 1.

9. An agricultural product according to claim 8, characterized in that the product is selected from the group consisting of bulbs, tubers, root-tubers, seed-potatoes, rootstocks, cuttings, grafts, onions, maize, wheat, coffee beans, cocoa beans, soy beans, seeds, berries, citrus fruits such as oranges, grapefruits and lemons, grapes, peaches, plums, cherries, cereal crops, vegetables, coffee plants, cocoa plants, fruit trees, grape plants, strawberries, cucumber plants, and tomato plants.

10. A process for the treatment of mold growth on a bulb which comprises adding an antifungal composition according to claim 1 to the bulb directly after harvesting of the bulb.

11. A composition according to claim 1, wherein the composition comprises 0.1 g/l to 3 g/l of natamycin and 2 g/l to 30 g/l of phosphite.

12. A composition according to claim 1, wherein the composition has a synergistic effect.

13. A composition according to claim 1, wherein the phosphite is present and is an alkali metal salt of phosphorous acid or an alkaline earth metal salt of phosphorous acid.

14. A composition according to claim 1, wherein the phosphite is present and is potassium phosphite, or sodium phosphite, or ammonium phosphite.

15. A synergistic fungicidal composition, comprising:
   I) a fungicidal component consisting of: a fungicide (a) and a fungicide (b):
   wherein fungicide (a) is natamycin; and
   wherein fungicide (b) is at least one selected from the group consisting of phosphorous acid, phosphite, and mixtures thereof, wherein the phosphite is selected from the group consisting of potassium phosphite, sodium phosphite, ammonium phosphite, an alkali metal salt of phosphorous acid, and an alkaline earth metal salt of phosphorous acid.

16. The synergistic fungicidal composition according to claim 15, wherein the phosphite is present and is an alkali metal salt of phosphorous acid or an alkaline earth metal salt of phosphorous acid.

17. The synergistic fungicidal composition according to claim 15, wherein the phosphite is present and is potassium phosphite, or sodium phosphite, or ammonium phosphite.

18. The synergistic fungicidal composition according to claim 15, further comprising:
   II) a surfactant component.

19. A process for the treatment of an agricultural product, which comprises adding a composition according to claim 15 to the agricultural product.

20. An agricultural product treated with a composition according to claim 15.

21. A synergistic fungicidal composition, comprising:
(a) natamycin, and
(b) phosphite, wherein the phosphite is selected from the group consisting of potassium phosphite, sodium phosphite, ammonium phosphite, an alkali metal salt of phosphorous acid, and an alkaline earth metal salt of phosphorous acid,
wherein said natamycin and phosphite are the only fungicides present in the composition.

22. The synergistic fungicidal composition according to claim 21, wherein the phosphite is potassium phosphite, or sodium phosphite, or ammonium phosphite.

23. The synergistic fungicidal composition according to claim 21, wherein the phosphite is an alkali metal salt of phosphorous acid or an alkaline earth metal salt of phosphorous acid.

\* \* \* \* \*